United States Patent [19]

Day et al.

[11] 4,083,225
[45] Apr. 11, 1978

[54] ON-LINE ULTRASONIC GAS ENTRAINMENT MONITOR

[75] Inventors: Clifford K. Day; Herbert N. Pedersen, both of Richland, Wash.

[73] Assignee: The United States of America Government as represented by the United States Department of Energy, Washington, D.C.

[21] Appl. No.: 667,924

[22] Filed: Mar. 17, 1976

Related U.S. Application Data

[63] Continuation-in-part of Ser. No. 508,004, Sep. 20, 1974, abandoned, which is a continuation of Ser. No. 360,699, May 15, 1973, abandoned.

[51] Int. Cl.² ............................................. G01N 29/02
[52] U.S. Cl. ............................................. 73/19
[58] Field of Search ............ 73/19, 67.8 R, 67.9, 73/69, 194 A, 24, 61 R; 310/8.2, 8.5, 8.6, 8.7

[56] References Cited

U.S. PATENT DOCUMENTS

| 2,573,390 | 10/1951 | Blanchard | 73/67.5 R |
|---|---|---|---|
| 3,028,752 | 4/1962 | Bacon | 73/67.8 R |
| 3,240,674 | 3/1966 | Ledwidge | 73/19 |
| 3,283,562 | 11/1966 | Hesig et al. | 73/19 |
| 3,290,934 | 12/1966 | Brown et al. | 73/194 A |
| 3,486,370 | 12/1969 | Chedeville et al. | 73/24 |
| 3,596,504 | 8/1971 | Frey | 73/67.8 R |
| 3,731,523 | 5/1973 | Vissers et al. | 73/19 |

OTHER PUBLICATIONS

Woodward et al.; *Ultrasonics*, "Some Aspects of Boiling Noise Detection in Sodium Reactors by Mech. Waveguides," 1/1971, pp. 21–25.

*Primary Examiner*—Richard C. Queisser
*Assistant Examiner*—Stephen A. Kreitman
*Attorney, Agent, or Firm*—D. C. Abeles; Z. L. Dermer

[57] ABSTRACT

Apparatus employing ultrasonic energy for detecting and measuring the quantity of gas bubbles present in liquids being transported through pipes. An ultrasonic transducer is positioned along the longitudinal axis of a fluid duct, oriented to transmit acoustic energy radially of the duct around the circumference of the enclosure walls. The back-reflected energy is received centrally of the duct and interpreted as a measure of gas entrainment.

One specific embodiment employs a conical reflector to direct the transmitted acoustic energy radially of the duct and redirect the reflected energy back to the transducer for reception. A modified embodiment employs a cylindrical ultrasonic transducer for this purpose.

2 Claims, 6 Drawing Figures

ON-LINE ULTRASONIC GAS ENTRAINMENT MONITOR

CROSS REFERENCES TO RELATED APPLICATIONS

This is a continuation in part of application Ser. No. 508,004, filed Sept. 20, 1974, which was a continuation of application Ser. No. 360,699, filed May 15, 1973, now both abandoned.

BACKGROUND OF THE INVENTION

The invention described herein was made in the course of, or under, a contract with the United States Atomic Energy Commission, and pertains generally to ultrasonic transducers and more specifically to ultrasonic transducers designed to monitor gas entrainment.

The theory and application of acoustical techniques to quantify voids or bubbles in liquids are rather well known in the art. Several unique techniques exist for this purpose. A transmission technique employs a measure of the total attenuation of an ultrasonic signal as it travels through the liquid being monitored. A scattering technique employs a measure of the degree of scattering reflected from voids passing through an acoustical beam. A third speed of sound technique measures the change in transmission times due to the differences in the speed of sound in voids as compared to liquids.

While these techniques have been successful in monitoring the presence of voids and quantifying them within the path of the acoustic beam, the present state of the art has not advanced to the stage where the total volume of liquid within a container can be monitored without employing an exhaustive number of transducers around the periphery of the liquid enclosure. Generally, a transducer is positioned at one location on the fluid container surface and a reflector is diametrically supported on the opposite container surface. The volume of liquid within the path of the acoustic beam is then monitored and the results extrapolated to cover the entire volume of liquid. While the resulting data has been satisfactory for most applications, precision measurements have not been able to be accommodated.

An accurate measure of the total volume of liquid would expand the capabilities of ultrasonics to more versatile applications in nuclear reactor systems such as sodium cooled breeder reactors. Such systems could then be employed to detect voids in the sodium coolant resulting from the release of fission gas during a fuel element failure; evidencing the fault.

Accordingly, a new acoustical device is desired having the capabilities of accurately measuring an entire volume of liquid enclosed within, or transported through a container.

SUMMARY OF THE INVENTION

Briefly, this invention employs acoustic energy to quantify voids in an enclosure containing or carrying liquids. Acoustic energy is generated at a central location within the container and directed radially outward towards the enclosure's walls around the entire circumference thereof. The energy reflected from the enclosure walls is then received and interpreted as a measure of the voids within the interior of the enclosure.

Accordingly, an entire volume of liquid is monitored at a central location within the container to give a total measure of voids at any given point in time.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

This invention employs properly arranged and modified commercially available ultrasonic apparatus for on-line measurement of gas entrainment (detection of small amounts of gas bubbles dispersed within a liquid). Generally, ultrasonic energy is generated at a central location within a liquid container and directed through the liquid radially of the container to the enclosure walls. The back-reflected signal is then received at the generating location and interpreted as a direct measurement of gas entrainment within the monitored volume.

Figure 1:
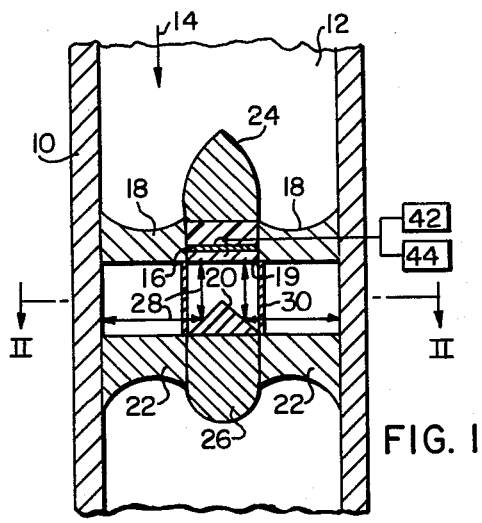
FIG. 1 is a longitudinal cross-sectional view of a fluid conduit incorporating the apparatus of this invention.

FIG. 1 illustrates one embodiment of the apparatus of this invention supported at a central location within the interior 12 of a cylindrical tubular fluid conduit 10. The arrow 14 indicates the direction of fluid flow, though it should be understood that fluid movement is not a necessary prerequisite to the operation of this invention. An ultrasonic transducer, piezoelectric, magnetostrictive or the like, is supported parallel to the axis of revolution of the fluid conduit, centered therearound by arms 18, formed integral with and extending radially from the enclosure walls. The transducer 16 is aligned to transmit pulsed ultrasonic energy along a path parallel to the central axis of the fluid conduit, as indicated by the directional arrows 28. A separate conical ultrasonic reflector 20 is spaced from and positioned in juxtaposed relationship to the transducer generating face 19, supported by radially extending arms 22, which form an integral part of the enclosure walls at the periphery of the conduit. The conical sides of the reflector are sloped at a 45° angle from the base and the apex is centered around the axis of revolution of the fluid duct in alignment with and opposite to the center of the transducer generating face 19. Flow baffles 24 and 26 are respectively positioned on opposite sides of the transducer/reflector assembly, designed in a manner to minimize turbulent fluid flow, which would otherwise result from the central positioning of the apparatus of this invention within the path of fluid movement. The support arms 18 and 22 are similarly designed for this purpose. Additionally, a cylindrical tubular housing or shell 30, constructed from ultrasonically transparent material is suspended between the supports 18 and 22, enclosing the transducer's generating face 19 and the conical reflector 20, thereby isolating the transducer/reflector assembly from the external fluid path in order to minimize resistance to the longitudinal motion of the fluid through the conduit.

Thus, in accordance with this invention, an electrical pulse, generated by the oscillator 42, is converted to an ultrasonic pulse (high frequency mechanical longitudinal vibration, i.e., a compressional wave packet) by the transducer 16. The ultrasonic pulse then travels through the transducer's coupling materials and through a fluid medium enclosed within the optional thin shell 30 supplied for flow improvement, to the conical reflector 20. The 45° reflector redirects the acoustic energy radially of the pipe towards the enclosure walls. The back-reflected energy is redirected by the reflector to the transducer where it is converted back to an electrical output. The output representative of the back-reflected energy is conducted by electrical leads, not shown, supported on or carried within the support arms 18 to processing and monitoring equipment 44 positioned exterior of the pipe 10. The decrease in the returned pulse height (attenuation of the ultrasonic intensity) is then a measure of the amount of obstacles or discontinuities (volume of gas bubbles) within the fluid stream.

Figure 2:
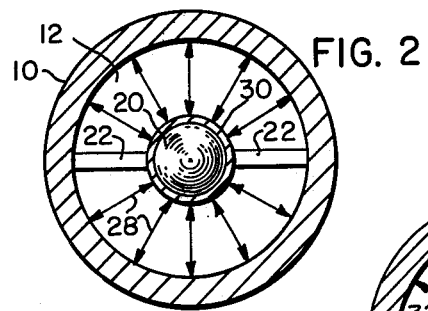
FIG. 2 is a cross-sectional view of the conduit of FIG. 1 taken along the lines II—II thereof.

FIG. 2 shows a cross-section of the piping assembly of FIG. 1 taken at the reflector assembly and better illustrates the radially directed acoustic energy and back-reflected energy from the enclosure walls. Thus, it can be seen that the entire volume of fluid is monitored to give an accurate determination of gas entrainment.

Figure 3:
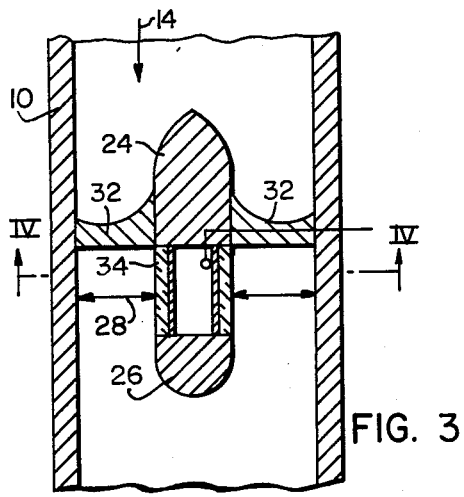
FIG. 3 is a longitudinal cross-sectional view of a fluid conduit incorporating a second embodiment of the apparatus of this invention.

FIG. 3 illustrates a second embodiment which can be employed to effect the teachings of this invention. The modification illustrated is similarly shown within the environment of a cylindrical tubular conduit 10 supported centrally within the conduit interior 12 by support arms 32 formed integral with and extending radially from the enclosure walls. A cylindrical ultrasonic transducer 34 is employed as a source of acoustic energy which is directed radially of the conduit as indicated by the directional arrows 28. The transducer is cantilevered from the support arms 32 and positioned to have its axis of revolution coincide with the central axis of the tubular conduit. Flow baffles 24 and 26 and the supporting arms 32 are designed in accordance with the direction of fluid flow 14 to minimize turbulence and reduce resistance in the direction of fluid movement 14.

Figure 4:
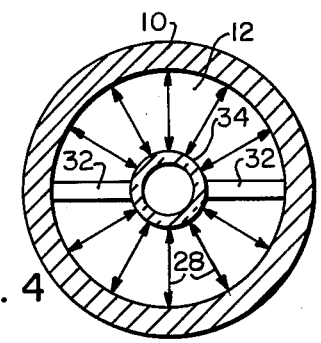
FIG. 4 is a cross-section view of the fluid conduit of FIG. 3 taken along the line IV—IV thereof.

Referring to FIG. 4 which shows a cross-sectional view of the transducer pipe assembly, it will be appreciated that the transducer directly radiates and receives the pulsed ultrasonic energy radially of the pipe covering the entire volume of fluid within a given pipe cross-section. As previously described, the acoustic energy reflected off the walls of the enclosure back to the transducer is converted to electrical form, then processed and analyzed by separate electronic apparatus positioned exterior of the piping.

Figure 6:
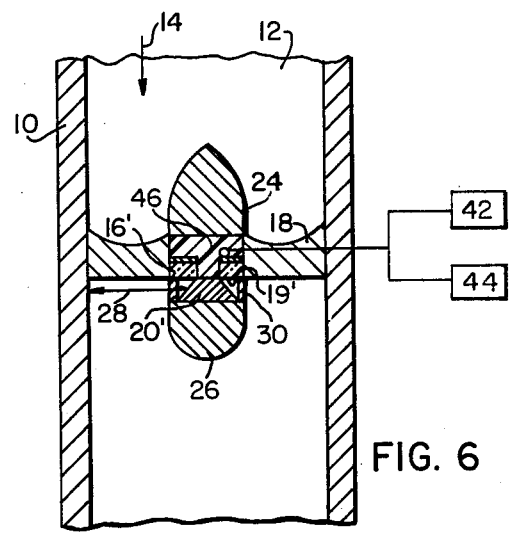
FIG. 6 is a longitudinal cross-sectional view of a fluid conduit incorporating a third embodiment of the apparatus of this invention.

FIG. 6 illustrates a third embodiment which can be employed to effect the teachings of this invention. The arrangement illustrated in FIG. 6 exhibits the advantage of each of the embodiments described above. The transducer 16', baffle arrangement 24, support structure 18 and instrumentation 42 and 44 are identical to the corresponding components illustrated in FIG. 1 except for the annular geometry of the piezoelectric element of the transducer 16'. The conical reflector 20' is truncated to mate with the annulus of the piezoelectric element. The reflector is supported at its mating interface with transducer generating face 19' by either a bonded or mechanical coupling such as a threaded connection. An acoustic damping material such as silicon rubber is desirably positioned within the annulus so that the effective generating face 19' directs the acoustic energy to reflect off the 45° incline of the reflector 20'. The cylindrical shell 30 and baffle 26 are identical to the design illustrated in FIG. 1, however the entire assembly is catilevered from a single support structure 18 as in FIG. 3, which reduces turbulence, without the necessity of employing a cylindrical generating fuse 34 which is not as structurally sound. The operation of the structure is identical to that described above with structural and fluid mechanical advantages achieved through a more compact design.

Bubble detection or quantification is accomplished by monitoring the signal corresponding to the pulses reflected off the pipe walls. Bubbles passing through the active region scatter the acoustic energy and produce an attenuated electrical signal in the output electronics. It is also possible to detect and quantify bubbles by monitoring the electrical pulses resulting from the acoustic energy directly reflected off the bubbles back to the transducer.

Thus, utilizing the apparatus described and contemplated by this invention, all bubbles traveling in the pipe must pass through the acoustic beam and will be detected if of sufficient diameter to scatter the incident energy. The smallest detectable diameter is determined by the acoustic signal frequency, however, large numbers of very small bubbles can also be sensed. While the transmission technique has been illustrated as one method of analyzing the information obtained from the apparatus of this invention, it should be realized that the scattering and speed of sound technique previously described can also be employed. Additionally, while the monitoring environment has been illustrated as a cylindrical tubular conduit, other geometrically-shaped conduits and containers can be accommodated by employing corresponding, suitably shaped transducers and reflectors.

Figure 5:
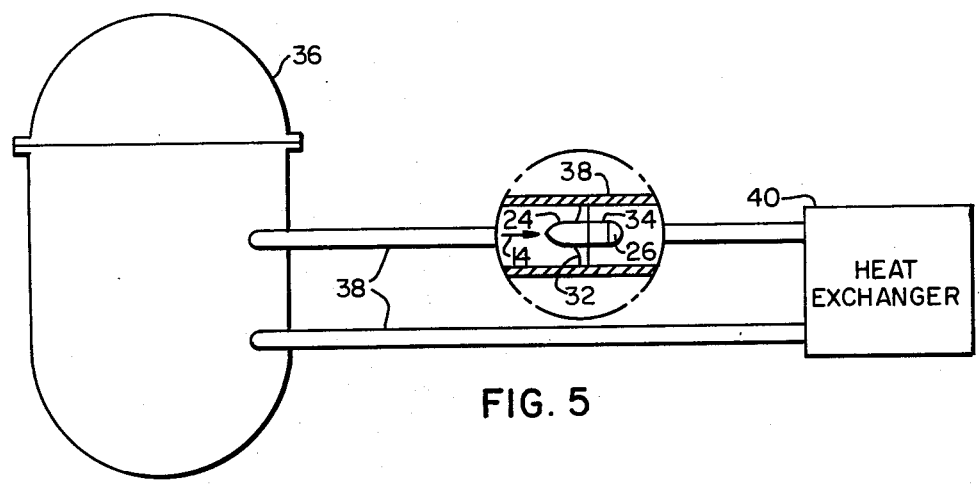
FIG. 5 is a schematic view of a reactor primary loop assembly incorporating the embodiment of FIG. 3.

Accordingly, the apparatus of this invention is specifically suitable for application as a fail fuel monitor for a liquid cooled reactor such as the reactor 36 illustrated in FIG. 5. The reactor is shown having primary coolant piping 38 formed integral with and extending from the reactor walls to a heat exchanger 40 normally employed in conjunction with steam generating apparatus in the commerical production of electricity. In such an application, it is merely necessary to form the piping 38 such that one section is constructed in accordance with the embodiments described as exemplary of this invention. The electrical output generated from the acoustic monitoring equipment of this invention can then be surveyed to give an indication of the presence of failed fuel within the interior of the reactor.

What is claimed is:

1. An acoustic device for quantifying bubbles in an elongated tubular enclosure confining a liquid, comprising:
    an acoustic transducer having an annular acoustic generating face sized to be supported centrally around the axis of revolution of the enclosure substantially spaced from the enclosure wall with the annular generating face of the transducer oriented to direct acoustic signals longitudinally within the enclosure; and
    a truncated conical acoustic reflector having the sides of the cone slope away from the base at a 45° angle with the plane section parallel to the base which replaces the apex of the cone coextensive and mating with and being supported by the annulus of the generating face of the transducer in a manner to direct the signal generated by the transducer radially outward towards the enclosure wall over a 360° arc around the circumference thereof and redirect received ultrasonic energy back reflected, along the line of initial reflection, to the transducer for reception, the transducer being responsive to the back reflected energy to provide an electrical output representative of the intensity of the back reflected signal.

2. The apparatus of claim 1 wherein the annulus of the generating face is acoustically damped.

* * * * *